US008026476B2

(12) United States Patent
Yamaguchi

(10) Patent No.: US 8,026,476 B2
(45) Date of Patent: Sep. 27, 2011

(54) MASS ANALYZING METHOD

(75) Inventor: Shinichi Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 324 days.

(21) Appl. No.: 12/307,857

(22) PCT Filed: Sep. 21, 2006

(86) PCT No.: PCT/JP2006/318708
§ 371 (c)(1),
(2), (4) Date: Jan. 7, 2009

(87) PCT Pub. No.: WO2008/035419
PCT Pub. Date: Mar. 27, 2008

(65) Prior Publication Data
US 2009/0309017 A1    Dec. 17, 2009

(51) Int. Cl.
H01J 49/42    (2006.01)
(52) U.S. Cl. .......................... 250/282; 435/6
(58) Field of Classification Search .................. 250/282; 435/6
See application file for complete search history.

(56) References Cited

U.S. PATENT DOCUMENTS

| 6,329,146 | B1 * | 12/2001 | Crooke et al. ............... 435/6 |
| 6,649,911 | B2 * | 11/2003 | Kawato ....................... 250/293 |
| 6,656,690 | B2 * | 12/2003 | Crooke et al. ............... 435/6 |
| 6,861,644 | B2 * | 3/2005 | Miseki ........................ 250/282 |
| 7,041,472 | B2 * | 5/2006 | Norioka et al. ............ 435/68.1 |
| 7,348,553 | B2 * | 3/2008 | Wang et al. ................. 250/282 |
| 7,409,296 | B2 * | 8/2008 | Colinge et al. .............. 702/19 |
| 7,529,630 | B2 * | 5/2009 | Yamaguchi et al. ......... 702/27 |
| 7,541,157 | B2 * | 6/2009 | Dive et al. .................. 435/7.21 |
| 7,544,931 | B2 * | 6/2009 | Yamaguchi et al. ........ 250/282 |
| 7,577,538 | B2 * | 8/2009 | Wang ........................... 702/85 |
| 7,589,318 | B2 * | 9/2009 | Bloomfield et al. ........ 250/282 |
| 7,763,846 | B2 * | 7/2010 | Yamaguchi et al. ........ 250/281 |
| 7,880,135 | B2 * | 2/2011 | Umemura .................... 250/281 |
| 2002/0102572 | A1 * | 8/2002 | Crooke et al. ................ 435/6 |

(Continued)

FOREIGN PATENT DOCUMENTS

JP    8-124519 A    5/1996

(Continued)

OTHER PUBLICATIONS

Japanese Office Action dated Jul. 5, 2011, issued in corresponding Japanese Patent Application No. 2008-535237.

*Primary Examiner* — David A Vanore
(74) *Attorney, Agent, or Firm* — Sughrue Mion, PLLC

(57) ABSTRACT

When the analyzer provides the mass and composition formula of the product ion, which is probably produced in the process of a dissociation, through the input unit, based on known information, a composition formula list is created in the database. When a product ion is obtained in an $MS^n$ analysis, the data processor checks whether or not the ion's mass exists in the composition formula list, and in the case where it does, the composition formula corresponding to the mass is determined. Then, based the mass difference between the precursor ion and product ion or other factors, the precursor ion's composition formula is deduced, and if it is possible to ultimately narrow down the candidates for the target ion's composition formula, the analysis is terminated. Accordingly, if the composition formula list is available, the refinement operation for the candidates for the composition formula can be omitted.

11 Claims, 4 Drawing Sheets

U.S. PATENT DOCUMENTS

| | | | |
|---|---|---|---|
| 2002/0150926 A1* | 10/2002 | Jindal et al. | 435/6 |
| 2004/0014140 A1* | 1/2004 | Erlanson et al. | 435/7.1 |
| 2004/0077019 A1* | 4/2004 | Gstach | 435/7.1 |
| 2004/0169138 A1 | 9/2004 | Ootake et al. | |
| 2007/0048752 A1* | 3/2007 | Yan et al. | 435/6 |
| 2010/0312487 A1* | 12/2010 | Yamaguchi | 702/23 |

FOREIGN PATENT DOCUMENTS

| | | |
|---|---|---|
| JP | 10-142196 A | 5/1998 |
| JP | 11-260310 A | 9/1999 |
| JP | 2001-249114 A | 9/2001 |
| JP | 2004-257922 A | 9/2004 |
| WO | 2006/049064 A1 | 5/2006 |

* cited by examiner

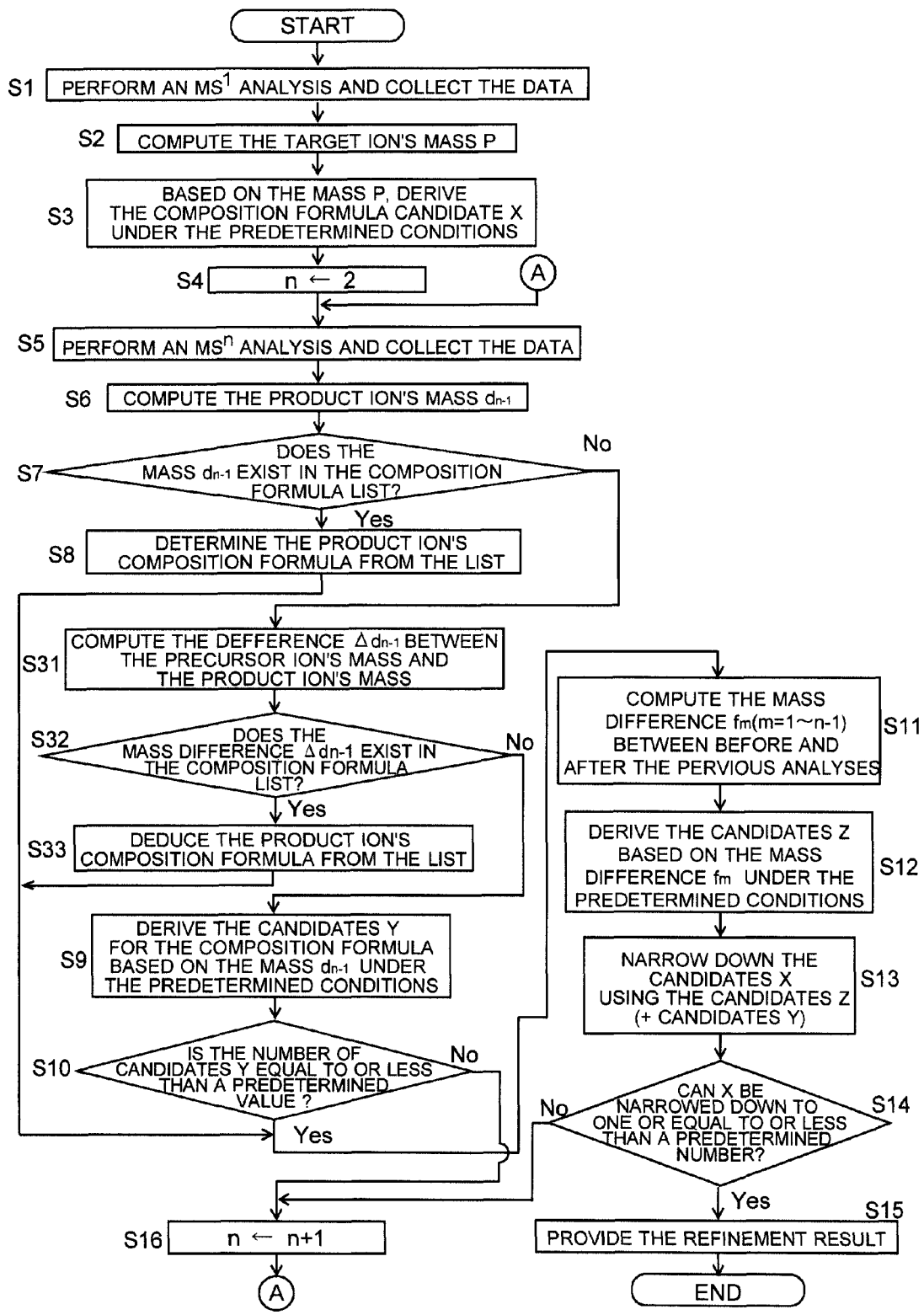

MASS ANALYZING METHOD

TECHNICAL FIELD

The present invention relates to a mass analyzing method for a mass spectrometer, and more precisely to a mass analyzing method using a mass spectrometer capable of analyzing a product ion or ions generated by dissociating an ion to be analyzed. In particular, it relates to a method for analyzing the composition and structure of a molecule.

BACKGROUND ART

In the field of mass analysis using an ion trap mass spectrometer or other apparatuses, a technique called the MS/MS analysis (or tandem analysis) has been recognized. In a general MS/MS analysis, an ion (target ion) having a specific mass-to-charge ratio (m/z) is first selected as a precursor ion from an object to be analyzed, and the precursor ion thus selected is dissociated by a collision-induced dissociation (CID) process. After that, a variety of product ions generated by the dissociation are mass analyzed to obtain the information on the mass and chemical structure of the target ion.

In recent years, samples having larger molecular weight than before have been analyzed with such an apparatus, and their chemical structures (compositions) have also tended to become more complicated. Hence, depending on the quality of the sample, ions are often not dissociated to have a sufficiently small mass by only a one-stage dissociation operation. In such cases, an $MS^n$ analysis may often be performed in which a dissociation operation is repeated multiple times (n−1 times) and the product ions finally generated are mass analyzed (refer to Patent Documents 1 and 2 for example). The mass analysis of a product ion by a single dissociation operation is an $MS^2$ analysis, and a normal mass analysis without a dissociation can be described as an $MS^1$ analysis.

In such an $MS^n$ analysis, the candidates for the molecular structure and composition of a target substance to be analyzed are narrowed down using basically both the composition formulae formed by the combination of elements deduced from the precursor ion's mass and the combinations of the elements deduced from the product ion's mass. However, even an apparatus capable of computing the mass with a certain level of high accuracy has the problem that, as the molecular weight of the target substance becomes larger, the refinement becomes more difficult and tends to leave more candidates, making it very difficult to ultimately determine the composition and structure of the target substance. In addition, if the number of candidates for a precursor ion and product ion is large during the process, it takes a very long time to perform an analysis to deduce the composition of the target substance.

[Patent Document 1] Japanese Unexamined Patent Application Publication No. H10-142196
[Patent Document 2] Japanese Unexamined Patent Application Publication No. 2001-249114

DISCLOSURE OF THE INVENTION

Problems to be Solved by the Invention

As previously described, conventional analyzing methods for a molecular structure and composition of a target substance have the following problems: although the analysis takes a long processing time, the obtained result is not sufficiently narrowed down. Hence, it is difficult to deduce the target substance's structure and composition. The present invention has been created to solve such problems, and the objective thereof is to provide a mass analyzing method capable of easily performing an analysis of the molecular structure and composition of a target substance with high accuracy, particularly in the case of a substance having a large molecular weight.

Means for Solving the Problems

To solve the previously described problems, the first aspect of the present invention provides a mass analyzing method, using a mass spectrometer capable of an $MS^n$ analysis in which a precursor ion originating from a target substance is dissociated for n−1 stages (where n is an integer equal to or more than two) and a product ion generated by a dissociation is mass analyzed, for performing an analysis of a molecular structure and composition of the target substance based on data collected by the mass spectrometer, including:

establishing a correspondence relationship, as preliminary information, between a specified mass and a composition formula, for a variety of ions generated in a dissociation process; checking whether or not the mass of a product ion obtained by an $MS^m$ (where m is an integer satisfying $2 \leq m \leq n$) analysis corresponds to a mass given by the preliminary information; and in the case where the result of the checking is positive, determining the composition formula of the product ion by using the preliminary information and then deducing the composition of the target substance.

In an embodiment of the first aspect of the present invention, after the data of an $MS^m$ analysis where m is 2, 3, ..., n, are collected, it is checked whether or not the mass of a product ion obtained by each analysis corresponds to a mass given by the preliminary information. That is, the measurements of necessary mass analyses are first performed to obtain all the data, and the preliminary information is used in performing an analysis processing based on the data.

In another embodiment of the first aspect of the present invention, each time an $MS^m$ analysis is performed in the increasing order of m as 2, 3, ..., it is checked whether or not the mass of a product ion obtained by the analysis corresponds to a mass given by the preliminary information. That is, while performing a mass analysis with a dissociation, it is checked whether or not the preliminary information can be applied to the obtained result. In the case where the deduction of the composition of the target substance can be appropriately performed based on the result, the measurement is terminated without performing any subsequent mass analysis in which the dissociation is performed for a larger number of stages.

Usually, the deduction of the composition of an ion having a large mass is performed with limitations on the kinds of constituent elements and the maximum number of these constituent elements. Generally, for a given mass, it is possible to find a plurality of composition formula's candidates each of which gives a mass close to the mass concerned, and sometimes the number of the candidates becomes large. On the other hand, depending on the original sample's kind and the purpose of the analysis, a portion of the target substance's structure (or composition) may be known and the approximate mass and composition of a product ion originating from this substance may also be known. For example, suppose that the target of the analysis is a by-product that is simultaneously produced in the process of producing a main product by a certain chemical reaction. In this kind of analysis, the main product and the by-product may have a similar structure including a common portion, and additionally the common portion's structure (or composition) may be known. In such a case, in the process of dissociating an ion, the common structure might be observed as a product ion (or a desorbed ion which will be described later).

Given this factor, in an analysis processing apparatus which realizes the mass analyzing method according to the first aspect of the present invention, when preliminary information is obtained by, for example, receiving each piece of data manually entered by a user or reading a set of data computed by another apparatus, the preliminary information is stored in a memory unit. In the process of performing mass analyses in series such as, $MS^1$ analysis, $MS^2$ analysis, . . . , it is sequentially checked whether or not the mass of the product ion corresponds to the mass stored in the memory unit. Then, in the case where the result of the checking is positive, the composition formula associated with the mass is determined to be the composition formula of the product ion. That is, in this case, it is no longer necessary to take the procedure of deriving a plurality of candidates for the composition formula from the mass of the product ion and then narrowing down the candidates.

In the case where the composition of the fragment (or desorbed ion) desorbed from a precursor ion in a dissociation operation, in addition to the mass of the product ion produced in the dissociation process, is known or can be previously deduced with high accuracy, it is possible to use the correspondence relationship between the mass and the composition formula of this desorbed ion. That is, the second aspect of the present invention has been created to solve the previously described problems provides a mass analyzing method, using a mass spectrometer capable of an $MS^n$ analysis in which a precursor ion originating from a target substance is dissociated for n–1 stages (where n is an integer equal to or more than two) and a product ion generated by a dissociation is mass analyzed, for performing an analysis of a molecular structure and composition of the target substance based on data collected by the mass spectrometer, including:

establishing a correspondence relationship, as preliminary information, between a specified mass and a composition formula, for a fragment desorbed in a dissociation process;

checking whether or not the difference between the mass of a precursor ion of an $MS^m$ (where m is an integer satisfying $2 \leq m \leq n$) analysis and the mass of a product ion obtained by the analysis corresponds to a mass given by the preliminary information; and in the case where the result of the checking is positive, determining the composition formula of the product ion by using the preliminary information and then deducing the composition of the target substance.

Similar to the first aspect of the present invention, the second aspect of the present invention also has two embodiments: In one embodiment, after data of an $MS^m$ analysis where m is 2, 3, . . . , n, are collected, it is checked whether or not the difference between the mass of a precursor ion in each analysis and the mass of a product ion obtained by the analysis corresponds to a mass given by the preliminary information. In the other embodiment, each time an $MS^m$ analysis is performed in the increasing order of m as 2, 3, . . . , it is checked whether or not the difference between the mass of a precursor ion in each analysis and the mass of a product ion obtained by the analysis corresponds to a mass given by the preliminary information.

EFFECTS OF THE INVENTION

In the mass analyzing method according to each of the first and second aspects of the present invention, by using known preliminary information, refinement of the product ions (i.e. the precursor ion of the mass analysis in the subsequent stage) can be omitted. Therefore, even in the case where the target substance's molecular weight is large, the number of candidates for the substance's composition formula is reduced and more reliable information can be provided to the user. The omission of a portion of the refinement process shortens the time required for the analysis processing to deduce the target substance's composition more than ever before.

As a matter of course, by combining the first and second aspects of the present invention, i.e. by combining the preliminary information presenting the correspondence relationship between the mass and composition formula of product ions and the preliminary information presenting the correspondence relationship between the mass and composition formula of desorbed fragments, the refinement of the product ions can be performed more easily and accurately.

BRIEF DESCRIPTION OF THE DRAWINGS

FIG. 5 is a flowchart illustrating an example of the procedure of a characteristic analysis processing operation using a mass spectrometer according to another embodiment.

| EXPLANATION OF NUMERALS | |
|---|---|
| 1 | Ion Source |
| 2 | Ion Trap |
| 21 | Ring Electrode |
| 22, 23 | End Cap Electrode |
| 24 | Ion Capture Space |
| 25 | Entrance Hole |
| 26 | Launching Hole |
| 27 | Voltage Generator |
| 28 | Gas Supply Source |
| 3 | TOFMS |
| 31 | Flight Space |
| 32 | Detector |
| 4 | Analysis Controller |
| 5 | Data Processor |
| 6 | Database |
| 61 | Library |
| 62 | Composition Formula List |
| 7 | Main Controller |
| 8 | Input Unit |
| 9 | Display Unit |

BEST MODE FOR CARRYING OUT THE INVENTION

Hereinafter, a mass analyzing method according to the present invention will be described with reference to the drawings.

Figure 1:
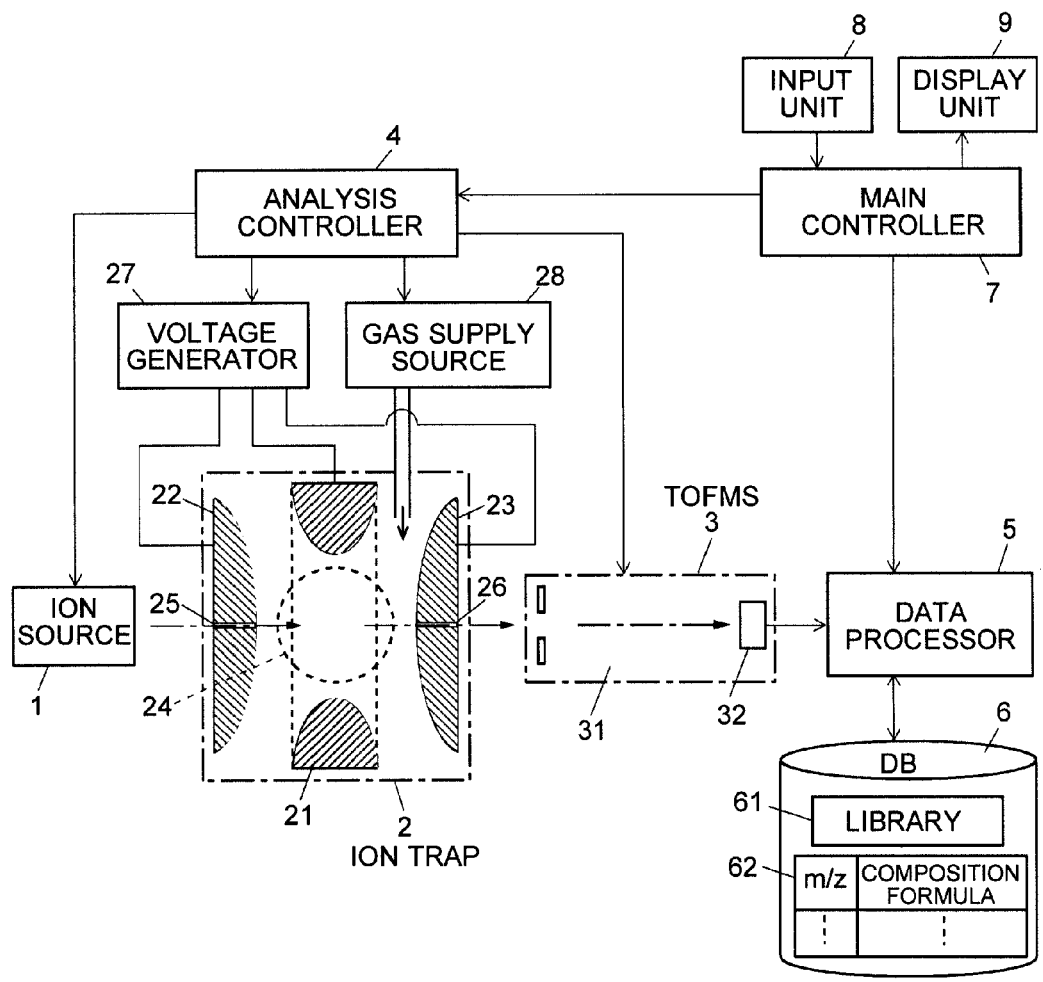
FIG. 1 is a schematic configuration diagram of the mass spectrometer according to an embodiment of the present invention.

FIG. 1 is a schematic configuration diagram of an embodiment of the mass spectrometer to perform the present invention. In FIG. 1, inside a vacuum chamber which is not shown, an ion source 1, ion trap 2, and time-of-flight mass spectrometer (which will be hereinafter called a TOFMS) 3 are provided. The ion trap 2 is composed of a ring electrode 21 and two end cap electrodes 22 and 23 facing each other. To the ring electrode 21, a radio-frequency high voltage is applied from a voltage generator 27. A quadruple electric field created in the space, which is surrounded by the ring electrode 21 and the pair of end cap electrodes 22 and 23, forms an ion capture space 24 to capture ions therein. On the other hand, to the end cap electrodes 22 and 23, an appropriate auxiliary alternating voltage in accordance with the analysis mode at the point in time is applied from the voltage generator 27. Inside the ion trap 2, a CID gas can be directed from a gas supply source 28 in order to accelerate the dissociation of the ions captured in the ion capture space 24. The operation of the ion source 1, TOFMS 3, voltage generator 27, gas supply source 28, etc. is controlled by an analysis controller 4.

In the mass spectrometer having the aforementioned configuration, the target sample is ionized in the ion source 1, and the ions generated are introduced into the ion trap 2 through an entrance hole 25. In the ion trap 2, the ions are temporarily captured in the ion capture space 24 by the electric field formed by the ring electrode 21 and end cap electrodes 22 and 23. After that, a CID gas is introduced into the ion trap 2 from the gas supply source 28, and the molecule of the gas is made to collide with the ions to accelerate the dissociation of the ions. After the sufficient dissociations, the voltages applied to the electrodes 21, 22, and 23 are changed to form an electric field for expelling the ions from the ion trap 2, and the ions are ejected through a launching hole 26. The ions expelled from the ion trap 2 fly in the flight space 31 of the TOFMS 3, and reach a detector 32 in the flight time in accordance with the mass-to-charge ratio. The detector 32 provides a detection signal according to the amount of the ions which sequentially reach the detector. A data processor 5 receives this detection signal to create a mass spectrum and performs, based on the mass of the peaks appearing on the mass spectrum, an analysis processing to deduce the target substance's molecular structure and composition, while referring to a library 61 and composition formula list 62 (which will be described later) stored in a database 6.

In this mass spectrometer, the ion trap 2 has the function of holding the ions having a specified mass-to-charge ratio and simultaneously dispersing the ions having an unnecessary mass-to-charge ratio to eliminate them. Hence, a mass analysis by multiple-stage dissociations, i.e. an $MS^n$ analysis with n more than two, can be performed by repeating the dissociation operation and ion selection in the following manner: after a dissociation by the CID is performed in the ion trap 2 as previously described, only the product ion having a predetermined mass-to-charge ratio is left in the ion trap 2, and then a CID dissociation is performed using this product ion as a precursor ion.

The mass spectrometer according to the present embodiment has a significant characteristic in the analysis processing operation in relation to such an $MS^n$ analysis. In this regard, an example of the procedure of the analysis processing operation will be described with reference to the flowchart of FIG. 3.

In the case where some compositions constituting the target substance are previously known from the target substance's kind and/or the analytical purpose, an analyzer (or user) enters the approximate masses and corresponding composition formulae of such compositions through the input unit 8. The information set at this point in time is stored in the database 6, as a composition formula list 62 in which masses and composition formulae are associated. This list corresponds to the preliminary information in the present invention.

When the analyzer indicates the initiation of an analysis through the input unit 8, a main controller 7 indicates the initiation of the analysis to an analysis controller 4. Under the control of the analysis controller 4, a normal mass analysis ($MS^1$ analysis) without a dissociation operation inside the ion trap 2 is first performed to collect the mass analysis data (Step S1). That is, after the ions generated in the ion source 1 are temporarily captured inside the ion trap 2, without a CID gas being introduced into the ion trap 2, the ions are expelled at predetermined timing through the launching hole 26 to be mass analyzed in the TOFMS 3 to obtain the data. The data processor 5 creates a mass spectrum from the mass data, finds the target ion's peak originating from the target substance from among the peaks appearing on the mass spectrum, and computes its mass P (Step S2).

Next, the data processor 5 refers to the database 6 and computes, from the target ion's mass P, the composition formula candidates X under the predetermined analysis conditions (Step S3). In the present embodiment, the analysis conditions may include the kind and maximum number of each atom (or element) selected as a possible component in accordance with the kind of target substance and other factors, the mass accuracy of the mass analysis, and so on. The number of composition formula candidates can be limited to some extent by the analysis conditions. However, if the analysis conditions are too severe, the actual composition formula might slip out from the candidates. Hence, the analysis conditions are required to be flexible to some extent. Due to this factor, particularly in the case where the target substance's molecular weight is large, the number of composition formula candidates tends to be too large.

Next, under the control of the analysis controller 4, the analysis repeat count parameter n is set to two and an $MS^n$ analysis is performed to collect the data (Steps S4 and S5). That is, the target substance which is the same as in the aforementioned $MS^1$ analysis is ionized in the ion source 1 and introduced into the ion trap 2. This time, one dissociation operation is performed inside the ion trap 2 with the target ion as the precursor ion, and the product ions generated by the dissociation are mass analyzed ($MS^2$ analysis) in the TOFMS 3. In this manner, the mass data of the product ion generated by an $MS^2$ analysis is obtained. Hence the data processor 5 creates a mass spectrum based on this data, finds the peak of the product ion among the peaks appearing on the mass spectrum, and computes its mass number $d_{n-1}$ (Step S6).

After the mass $d_{n-1}$ of the product ion is obtained, it is determined whether or not this mass $d_{n-1}$ exists in the composition formula list 62 (Step S7). However, in some cases, the values do not perfectly match due to the mass accuracy and other factors. Therefore, some tolerance is allowed for determining whether or not a corresponding mass exist in the composition formula list 62. If a corresponding mass exists in the composition formula list 62, the composition formula corresponding to the mass is determined to be the product ion's composition formula (Step S8). On the other hand, if a corresponding mass does not exist in the composition formula list 62, the library 61 in the database 6 is referred to, and the candidates Y for the product ion's composition formula are computed from the mass $d_{n-1}$ under the predetermined conditions (Step S9). The analysis conditions used in this step are generally the same as used in the previously described process for the parent ion. However, it is possible to appropriately change the analysis conditions in accordance with the knowledge based on the analysis results in the past or other factors.

Next, whether or not the number of candidates Y is equal to or less than a predetermined value is determined (Step S10), and in the case where it exceeds the predetermined value, the process proceeds to Step S16 which will be described later. On the other hand, in the case where the number of candidates Y is equal to or less then the predetermined value, or in the case where the product ion's composition formula has been determined in Step S8, the difference $f_m$ of the masses obtained before and after the previous analysis is computed (Step S11). That is, in the case where n=2, the mass difference $f_1$ between the precursor ion's mass P, which is the result of the $MS^1$ analysis, and the product ion's mass $d_1$, which is the result of the $MS^2$ analysis, is computed. Then, with reference to the library 61, the candidates Z for the desorbed ion's composition formula corresponding to the mass difference $f_1$ are computed under the predetermined conditions (Step S12).

After that, in accordance with a predetermined algorithm, the refinement of the candidates X for the composition formula for the original ion is performed by using the product ion's determined composition formula and the desorbed ion's composition formula candidates Z, or by using the composition formula's candidates Y and Z (Step S13). Then, it is determined whether or not the candidates X have been narrowed down to one, or equal to or less than the predetermined number of candidates (Step S14). In the present embodiment, the predetermined number can be appropriately determined; however, it may be preferably several at most, but usually a few, in view of providing appropriate information to the analyzer. In the case where it is determined that an appropriate refinement has been performed in Step S14, the result is provided through the display monitor of the display unit 9 or other devices (Step S15).

In the case where it is determined in Step S14 that the candidates have not been narrowed down to one or equal to or less than the predetermined number of candidates, the analysis repeat count parameter n is incremented (Step S16) and the process returns to Step S5. Also in the case where the number of candidates Y has exceeded the predetermined value in Step S10 as described earlier, the process returns to Step S5 via Step S16. When the process returns to Step S5, under the control of the analysis controller 4, the number of the dissociation operation inside the ion trap 2 is increased as previously described (e.g. in the case where n=3, two dissociation operations are performed), and the product ion obtained as the result is mass analyzed. Then, the subsequent processes are executed in the manner as previously described.

In the mass spectrometer according to the present embodiment, the composition formula list 62 is appropriately set in advance. Therefore, the number of executions of the refinement process is small and it is easy to deduce the target ion's composition formula, i.e. the target substance to be analyzed, with high accuracy and with a small number of analyses.

Figure 4:
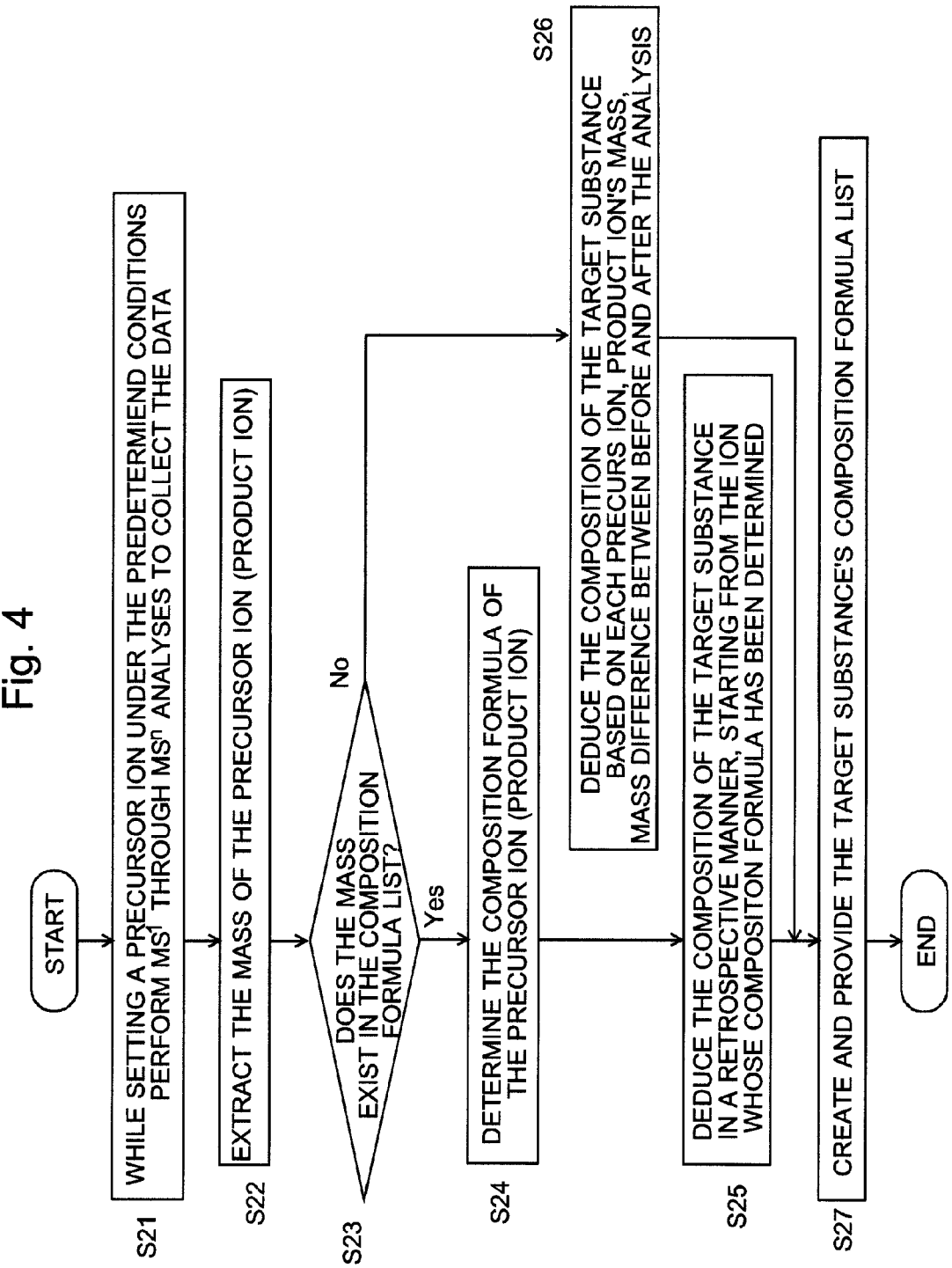
FIG. 4 is a flowchart illustrating an example of the procedure of a characteristic analysis processing operation in another embodiment.

In the mass spectrometer according to the aforementioned embodiment, the refinement of the composition formula is performed based on the data obtained by each analysis, while the analyses are being carried out. However, an analysis may be performed a preset number of times, i.e. $MS^1$ through $MS^n$ analyses for the predetermined n (e.g. n=5 or 6) may be performed, to obtain all the mass data for each analysis, and then an analysis processing may be performed for the collected data to deduce the target substance's (or target ion's) composition formula. FIG. 4 is a flowchart illustrating the procedure of this mode of analysis processing.

First, while setting the precursor ion in sequence under predetermined conditions, $MS^1$ through $MS^n$ analyses are performed to collect the mass data (Step S21). Concretely speaking, for example, in the case where a plurality of peaks appear on the mass spectrum obtained by performing an $MS^m$ analysis, the peak having the highest intensity is selected to be the precursor ion. After that, an analysis processing is performed: first, the mass of the precursor ion (or product ion in each stage) is extracted (Step S22), and it is determined whether or not one or some of these masses correspond to a mass in the composition formula list 62 (Step S23). If the composition formula list 62 has a pertinent mass, the composition formula corresponding thereto is determined to be the composition formula of the precursor ion (or product ion) (Step S24). Ultimately, starting from this ion whose composition formula has been determined, it is possible to determine the composition formula of the target ion or substance in a retrospective manner, i.e. by taking into account the mass difference between before and after each analysis as previously described (Step S25).

On the other hand, in the case where it has been determined that there is no corresponding mass in the composition formula list 62 in Step S23, the composition is deduced in series from the precursor ion's (or product ion's) mass, the mass difference between before and after the analysis, etc, and the composition formula of the target ion or target substance is ultimately deduced (Step S26). If one or plural candidates for the composition formula of the target substance are obtained, these are displayed as a list on the display unit 9 (Step S27).

In the aforementioned embodiment, a composition formula list 62 is created in which the masses and composition formulae of product ions are associated. Furthermore, the relationship between the mass and composition formula of desorbed ion which desorbs in association with a dissociation may be added to the list. Using this additional information makes the refinement of the product ion easier. An example of the procedure of an analysis processing operation in such an embodiment is illustrated in FIG. 5. Since this analysis processing operation is similar to the process explained with FIG. 3, the same processes are indicated with the same step numbers and the explanations are omitted. As characteristic processes, Steps S31 through S33 are added.

That is, in the case where the mass corresponding to the product ion's mass does not exist in the composition formula list 62 in Step S7, the difference $\Delta d_{n-1}$ between the mass of the precursor ion and that of the product ion in the preceding analysis is calculated in the next step (i.e. Step S31). The mass difference $\Delta d_{n-1}$ can be regarded as the mass of the fragment (which is called a desorbed ion in this embodiment) desorbed from the precursor ion in association with a dissociation, and whether or not this mass exists in the composition formula list 62 is determined (Step S32). In the case where a corresponding mass exists in the composition formula list 62, the product ion's composition formula is deduced based on the composition formula of the desorbed ion corresponding to the mass (Step S33), and the process proceeds to Step S11. On the other hand, in the case where no corresponding mass exists in the composition formula list 62, the process proceeds to Step S9.

Even in the case where the composition formula of the product ion itself is not found in the composition formula list 62, if the desorbed fragment's composition formula is known, the product ion's composition formula can be deduced with high accuracy by using the desorbed fragment's composition formula and a number of candidates for the precursor ion's composition formula. Accordingly, in the analysis processing method according to the present embodiment, the refinement of the target substance's composition formulae is much easier than that in the previously described embodiment.

As illustrated in FIG. 4, a known composition formula corresponding to the difference between the precursor ion's mass and the product ion's mass can also be used in the method in which $MS^1$ through $MS^n$ analyses are performed in advance to collect the mass data of each analysis, and then an analysis processing is performed for each collected data in order to deduce the target substance's composition formula. Obviously, this makes the refinement of the target substance's composition formula much easier.

Figure 2:
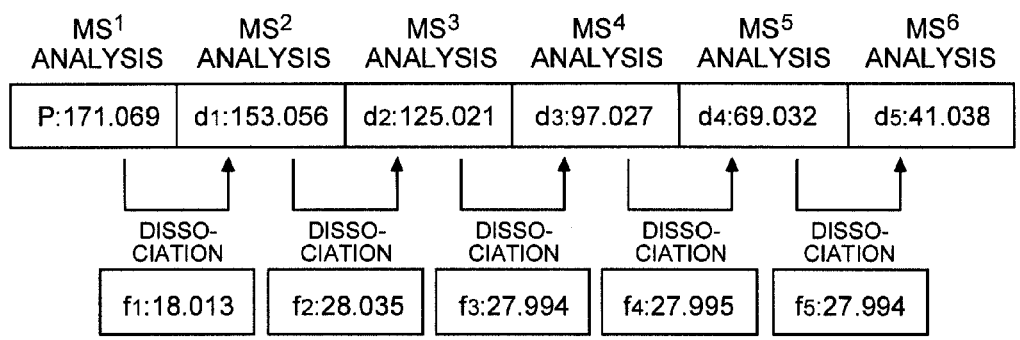
FIG. 2 is a pattern diagram illustrating a concrete example of an analysis processing operation.

Next, a concrete example of the aforementioned analysis processing will be explained with reference to FIG. 2. In this embodiment, it is presumed that the target ion's mass P is 171.066 (u: atomic mass unit), and in performing five dissociation processes with the ion as a precursor ion, the masses of the product ions obtained in the five dissociation operations are $d_1=153.056$, $d_2=125.021$, $d_3=97.027$, $d_4=69.032$, and $d_5=41.038$, respectively. In this case, the mass difference $f_m$ between the mass of the precursor ion and that of the product ion in an $MS^m$ analysis is as illustrated in FIG. 2. Table 1 illustrates the candidates for the composition formula which are lined up based on the $MS^1$ analysis' result, i.e. the target ion's mass P, under the following analysis conditions: atom's kind and maximum number of carbon (C):14, hydrogen (H): 30, oxygen (O):10, and nitrogen (N):10, and the mass accuracy of 0.02 u.

TABLE 1

| # | Mass | Diff. | Formula |
|---|------|-------|---------|
| 1 | 171.068 | 0.001 | $C_{11}H_9NO$ |
| 2 | 171.067 | 0.002 | $C_9H_7N_4$ |
| 3 | 171.072 | 0.003 | $H_9N_7O_4$ |
| . | . | . | . |
| . | . | . | . |
| . | . | . | . |
| 27 | 171.049 | 0.020 | $CH_3N_{10}O$ |

That is, a considerable number of composition formula's candidates X are lined up. If the mass accuracy is extremely high, to be more precise for example, if the condition that [Diff] in Table 1 is 0.001 can be set, it is possible to narrow down to one candidate (#1 in Table 1). However, the mass accuracy of actual mass spectrometers cannot be higher than ppm levels. Hence it is inevitable that a considerable number of candidates appear as previously described.

Next, the candidates for the composition formula based the $MS^2$ analysis, i.e. the product ion's mass $d_1$ after one dissociation operation under the aforementioned analysis conditions are lined up as illustrated in Table 2.

TABLE 2

| # | Mass | Diff. | Formula |
|---|------|-------|---------|
| 1 | 153.055 | 0.001 | $C_8H_9O_3$ |
| 2 | 153.058 | 0.002 | $C_{11}H_7N$ |
| 3 | 153.054 | 0.002 | $C_6H_7N_3O_2$ |
| . | . | . | . |
| . | . | . | . |
| . | . | . | . |
| 24 | 153.075 | 0.019 | $C_3H_{11}N_3O_4$ |

Also in this case, a similar number of candidates appear as have been computed from the target ion's mass P, and determining the composition formula is difficult. Therefore, in the aforementioned embodiment, the analysis is required to proceed to the $MS^3$ analysis or further ahead. In actuality, Table 3 illustrates the composition formula's candidates listed in the same manner from the product ion's mass $d_5$ after performing five dissociation operations for example. The number of candidates has been considerably decreased to two.

TABLE 3

| # | Mass | Diff. | Formula |
|---|------|-------|---------|
| 1 | 41.039 | 0.001 | $C_3H_5$ |
| 2 | 41.027 | 0.011 | $C_2H_3N$ |

This is because the product ion's mass $d_5$ has become dramatically small in comparison to the target ion's mass P, due to the repeated dissociation operations.

Table 4 illustrates the candidates for the desorbed ion for $f_3$, $f_4$, and $f_5$, whose mass difference is substantially the same.

TABLE 4

| # | Mass | Diff. | Formula |
|---|------|-------|---------|
| 1 | 27.995 | 0.001 | CO |
| 2 | 28.006 | 0.012 | $N_2$ |

However, from various findings it is generally accepted that the $N_2$ ion cannot be desorbed in an ion's dissociation phenomenon. Accordingly, by giving the information based on such knowledge in advance, the composition formula of $N_2$ can be excluded, and CO is obtained as a pertinent result.

Similarly, Tables 5 and 6 illustrate the candidates for the desorbed ion for the mass differences $f_2$ and $f_1$, respectively.

TABLE 5

| # | Mass | Diff. | Formula |
|---|------|-------|---------|
| 1 | 28.031 | 0.004 | $C_2H_4$ |
| 2 | 28.019 | 0.016 | $CH_2N$ |

TABLE 6

| # | Mass | Diff. | Formula |
|---|------|-------|---------|
| 1 | 18.011 | 0.000 | $H_2O$ |

Figure 3:
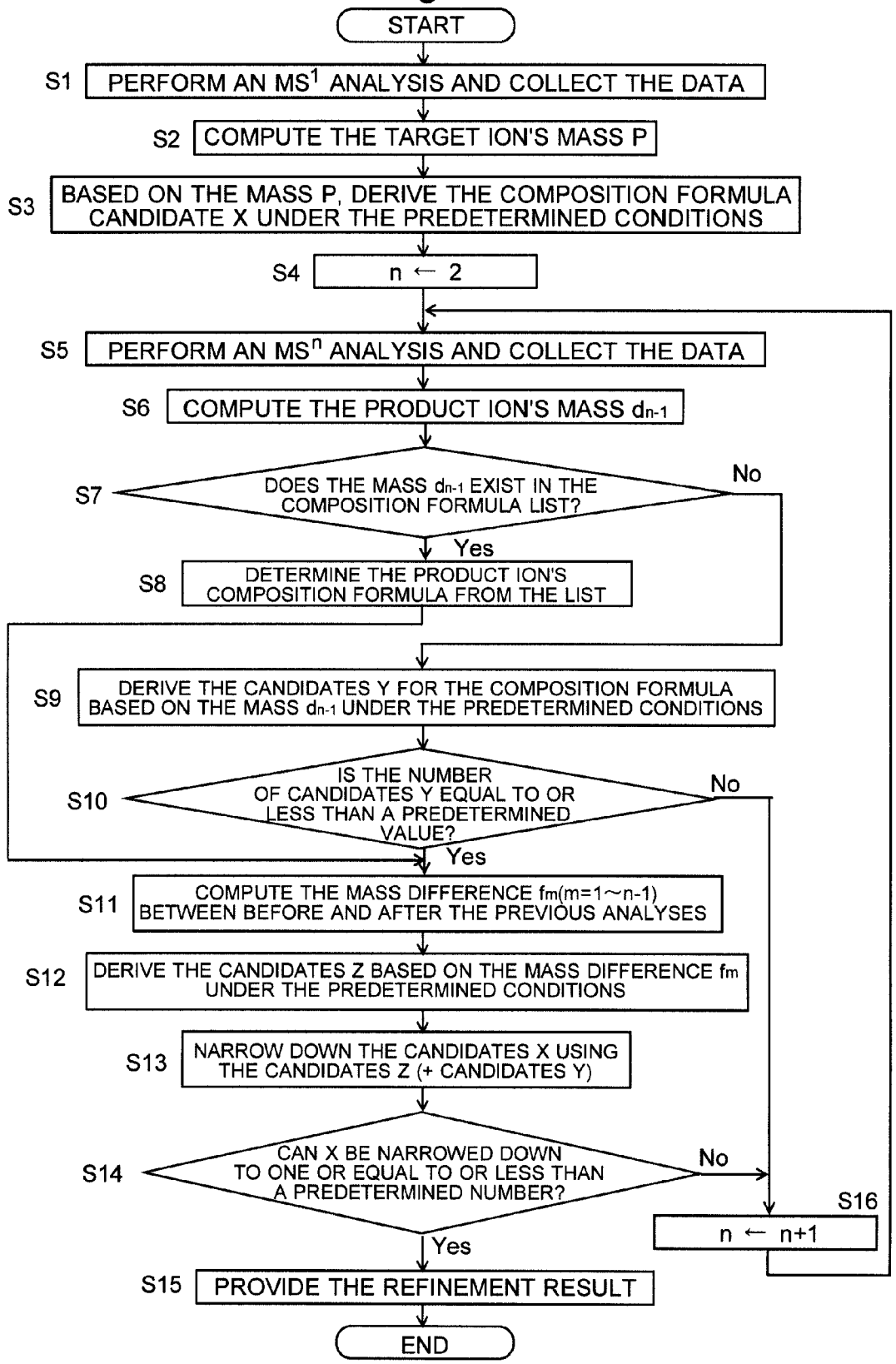
FIG. 3 is a flowchart illustrating an example of the procedure of a characteristic analysis processing operation using the mass spectrometer according to the present embodiment.

In view of the flowchart of FIG. 3, if for example the predetermined value in Step S10 is set to two or three, the determination result in Step S10 will be "Yes" after the execution of the $MS^6$ analysis, and the mass differences $f_1$ through $f_5$ are calculated to derive each candidate for the desorbed ion as previously described. The candidates Y in FIG. 3 are those illustrated in Table 3, and the candidates Z are those illustrated in Tables 4, 5, and 6. From these results, it is possible to express the original target ion P's composition formula's candidates as follows:

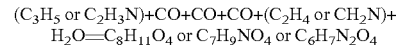

Hence, the original twenty-seven candidates can be narrowed down to three candidates. By displaying this refinement result on the display monitor of the display unit 9 for example, it is possible to provide important information for the analyzer to ultimately determine the composition formula.

Suppose the case where a product ion adjacent to the mass 153 obtained from this kind of sample can be determined to be $C_{11}H_7N$ from a piece of known information and this is stored in the composition formula list 62. In this case, the determination result will be "Yes" at the point in time when the product ion's mass $d_1$, which is a result of the $MS^2$ analysis, is determined in Step S7. That is, the composition formula #2 in Table 2 is determined. Since this signifies that the target ion P's composition formula certainly includes $C_{11}H_7N$, from among a number of composition formula candidates listed in Table 1, $C_{11}H_9NO$ is promptly extracted as a pertinent composition formula. Consequently, the $MS^3$ and subsequent analyses will no longer need to be performed, and the analysis processing time is short, which enhances the analysis' throughput. Of course, since the candidates for the target ion's composition formula are narrowed down to one, the analyzer is no longer required to make a self-judgment.

It should be noted that the embodiment described thus far is merely an example of the present invention, and that any modification, adjustment, addition or the like appropriately made within the spirit of the present invention is also covered within the scope of the present invention.

The invention claimed is:

1. A mass analyzing method, using a mass spectrometer capable of an $MS^n$ analysis in which a precursor ion originating from a target substance is dissociated for n−1 stages (where n is an integer equal to or more than two) and a product ion generated by a dissociation is mass analyzed, for performing an analysis of a molecular structure and composition of the target substance based on data collected by the mass spectrometer, comprising:
   establishing preliminary information for a variety of ions generated in a dissociation process based on previously known information of the target substance, the preliminary information being a correspondence relationship between a specified mass and a composition formula derivable from the target substance;
   checking whether or not a mass of a product ion obtained by an $MS^m$ (where m is an integer satisfying $2 \leq m \leq n$) analysis corresponds to the specified mass given by the preliminary information; and
   in a case where a result of the checking is positive, determining a composition formula of the product ion by using the preliminary information and then deducing a composition of the target substance.

2. The mass analyzing method according to claim 1, wherein
   after data of an $MS^m$ analysis where m is 2, 3, . . . , n, are collected, it is checked whether or not a mass of a product ion obtained by each analysis corresponds to a mass given by the preliminary information.

3. The mass analyzing method according to claim 1, wherein
   each time an $MS^m$ analysis is performed in an increasing order of m as 2, 3, . . . , it is checked whether or not a mass of a product ion obtained by the analysis corresponds to a mass given by the preliminary information.

4. The mass analyzing method according to claim 1, wherein
   in a case where the mass of the product ion obtained by the $MS^m$ analysis does not correspond to a mass given by the preliminary information, a library in a database under a predetermined analysis condition is referred to, and a candidate for a composition formula of the product ion is obtained based on the mass of the product ion obtained by the $MS^m$ analysis.

5. The mass analyzing method according to claim 4, wherein
   the predetermined analysis condition includes a kind and maximum number of each atom as a possible component.

6. The mass analyzing method according to claim 4, wherein
   a number of candidates for a composition formula of the product ion is determined, and in a case where the number exceeds a predetermined value, based on a mass of a product ion obtained by an $MS^m$ analysis in which m has been increased, a composition formula of the product ion is deduced.

7. A mass analyzing method, using a mass spectrometer capable of an $MS^n$ analysis in which a precursor ion originating from a target substance is dissociated for n−1 stages (where n is an integer equal to or more than two) and a product ion generated by a dissociation is mass analyzed, for performing an analysis of a molecular structure and composition of the target substance based on data collected by the mass spectrometer, comprising:
   establishing preliminary information for a fragment desorbed in a dissociation process based on previously known information of the target substance, the preliminary information being a correspondence relationship between a specified mass and a composition formula derivable from the target substance;
   checking whether or not a difference between a mass of a precursor ion of an $MS^m$ (where m is an integer satisfying $2 \leq m \leq n$) analysis and the specified mass of a product ion obtained by the analysis corresponds to a mass given by the preliminary information; and
   in a case where a result of the checking is positive, determining a composition formula of the product ion by using the preliminary information and then deducing a composition of the target substance.

8. The mass analyzing method according to claim 7, wherein
   after data of an $MS^m$ analysis where m is 2, 3, . . . , n, are collected, it is checked whether or not a difference between a mass of a precursor ion in each analysis and a mass of a product ion obtained by the analysis corresponds to a mass given by the preliminary information.

9. The mass analyzing method according to claim 7, wherein
   each time an $MS^m$ analysis is performed in an increasing order of m as 2, 3, . . . , it is checked whether or not a difference between a mass of a precursor ion in each analysis and a mass of a product ion obtained by the analysis corresponds to a mass given by the preliminary information.

10. The mass analyzing method according to claim 7, wherein
    in a case where the difference between the mass of the precursor ion obtained by the $MS^m$ analysis and the mass of the product ion obtained by the analysis does not correspond to a mass given by the preliminary information, a library in a database under a predetermined analysis condition is referred to, and a candidate for a composition formula of the product ion is obtained from a mass difference.

11. The mass analyzing method according to claim 10, wherein
    the predetermined analysis condition includes a kind and maximum number of each atom as a possible component.

* * * * *